(12) United States Patent
Svensson et al.

(10) Patent No.: US 9,763,618 B2
(45) Date of Patent: Sep. 19, 2017

(54) PALPOMETER

(75) Inventors: Peter Svensson, Risskov (DK); Gert Ravnholt, Ega (DK); Kirsten Ravnholt, legal representative, Ega (DK)

(73) Assignee: Sunstar Suisse SA, Etoy (CH)

( * ) Notice: Subject to any disclaimer, the term of this patent is extended or adjusted under 35 U.S.C. 154(b) by 440 days.

(21) Appl. No.: 13/520,817

(22) PCT Filed: Jan. 7, 2011

(86) PCT No.: PCT/DK2011/050006
§ 371 (c)(1),
(2), (4) Date: Jul. 15, 2013

(87) PCT Pub. No.: WO2011/082712
PCT Pub. Date: Jul. 14, 2011

(65) Prior Publication Data
US 2013/0296736 A1 Nov. 7, 2013

Related U.S. Application Data

(60) Provisional application No. 61/293,299, filed on Jan. 8, 2010.

(51) Int. Cl.
*A61B 5/00* (2006.01)
*A61B 5/103* (2006.01)

(52) U.S. Cl.
CPC .......... *A61B 5/4827* (2013.01); *A61B 5/0053* (2013.01); *A61B 5/103* (2013.01);
(Continued)

(58) Field of Classification Search
CPC .... A61B 5/0053; A61B 5/4824; A61B 5/4827
See application file for complete search history.

(56) References Cited

U.S. PATENT DOCUMENTS 2,551,487 A * 5/1951 Crowley ........................ 73/744
3,745,989 A * 7/1973 Pinna ..................... A61B 5/489
600/481

(Continued)

FOREIGN PATENT DOCUMENTS

DE 101 26 690 A1 7/2002
GB 2190750 A * 11/1987 ............. G01L 17/00
WO 2004/045408 A1 6/2004

OTHER PUBLICATIONS

Hardy, The Nature of Pain, Journal of Chronic Diseases, 4(1): 22-51, 1956.

*Primary Examiner* — Devin Henson
*Assistant Examiner* — Matthew Kremer
(74) *Attorney, Agent, or Firm* — Dinsmore & Shohl LLP

(57) ABSTRACT

A palpometer device for assisting an examiner to evaluate deep pain sensitivity in a patient includes a housing supporting an axially displaceable spring-biased probe having a proximal end extending from an axial bore in a proximal axial face of the housing, and adapted for abutting contact with the patient. Within the housing, the spring-biased probe incorporates an annular flange for engaging one end of a bias spring coaxially disposed within the housing. The bias spring is disposed coaxially about the probe to resist axial displacement of the housing towards the proximal end of the probe upon manual application of a bias force to the housing, when the proximal end of the probe is in contact with a patient's body.

13 Claims, 4 Drawing Sheets

(52) U.S. Cl.
CPC .......... *A61B 5/4824* (2013.01); *A61B 5/4528* (2013.01); *A61B 2560/0425* (2013.01)

(56) References Cited

U.S. PATENT DOCUMENTS

| | | | | |
|---|---|---|---|---|
| 3,874,369 | A | * | 4/1975 | Pannier et al. ............... 600/487 |
| 4,505,278 | A | * | 3/1985 | Alban .......................... 600/587 |
| 4,526,030 | A | * | 7/1985 | Vecera, Jr. ................... 73/146.8 |
| 4,641,661 | A | * | 2/1987 | Kalarickal .................... 600/557 |
| 4,800,896 | A | * | 1/1989 | Jalowayski ................... 600/572 |
| 4,838,280 | A | * | 6/1989 | Haaga .......................... 600/564 |
| 4,884,175 | A | * | 11/1989 | Weng ...................... G01L 17/00 362/116 |
| 5,230,348 | A | * | 7/1993 | Ishibe et al. .................. 600/585 |
| 2001/0037050 | A1 | * | 11/2001 | Lemperle ..................... 600/135 |
| 2003/0167021 | A1 | * | 9/2003 | Shimm ......................... 600/554 |
| 2008/0097236 | A1 | | 4/2008 | Kuban |

* cited by examiner

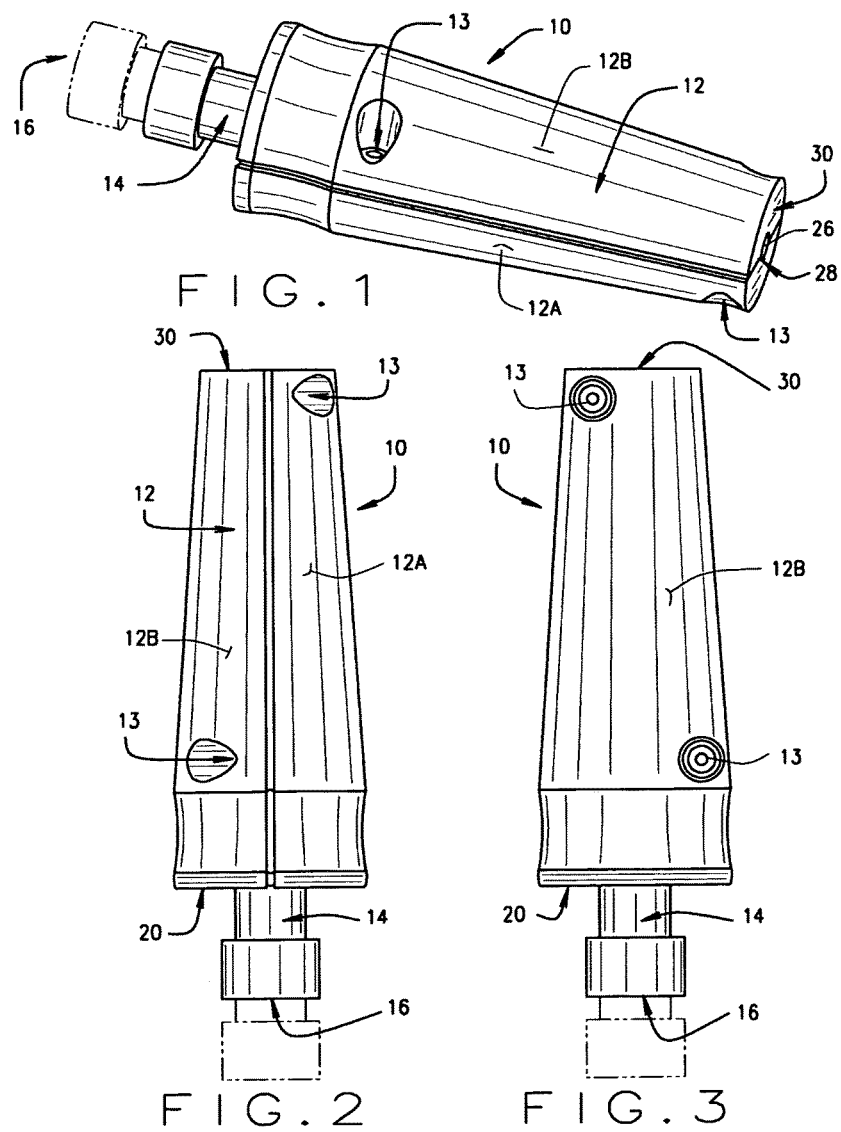

PALPOMETER

CROSS-REFERENCE TO RELATED APPLICATIONS

The present application is the U.S. national stage of PCT/DK2011/050006 filed Jan. 7, 2011, which claims priority of U.S. Provisional Patent Application Ser. No. 61/293,299 filed on Jan. 8, 2010, and which is herein incorporated by reference.

BACKGROUND OF THE INVENTION

The present application is related to methods and apparatus for the assessment of deep pain sensitivity in a patient, and in particular, to a manually actuated palpometer utilized to establish stimulus-response functions on the temporalis and masseter muscles and on the temporomandibular joint using a spring-biased probe configured to provide a uniform and repeatable stimulation to a patient.

Reliable assessment of deep pain sensitivity is needed for accurate diagnoses of patient sensitivity such as by dentists evaluating temporomandibular disorders (TMD) or doctors evaluating arthritis. Current methods and procedures rely either upon manual palpation by an examiner, or on the use of commercial esthesiometers or electronic pressure algometers. Manual palpation may lack accuracy and repeatability, as the examiner may not be able to provide consistent applications of pressure at various locations on the patient's body. The use of commercial esthesiometers or electronic pressure algometers requires expensive equipment which may not be available to all examiners.

Accordingly, it would be advantageous to develop an easily applicable, manually actuated, palpometer for clinical use, capable of applying a highly repeatable pressure to a selected area on a patient in order to assist an examiner in improving palpation procedures for touch and pain sensitivity.

BRIEF SUMMARY OF THE INVENTION

Briefly stated, the present disclosure provides a palpometer device (10) for assisting an examiner to evaluate deep pain sensitivity in a patient. The palpometer device (10) of the present disclosure includes a housing (12) supporting an axially displaceable spring-biased probe (14) having a proximal end (16) extending from an axial bore (18) in a proximal axial face (20) of the housing, and adapted for abutting contact with the patient. Within the housing (12), the spring-biased probe (14) incorporates an annular flange (22) for engaging one end of a bias spring (24) coaxially disposed within the housing. The bias spring (24) is disposed about the probe (14) to resist axial displacement of the housing (12) towards the proximal end (16) of the probe upon manual application of a bias force to the housing, when the proximal end (16) of the probe (14) is in contact with a surface of the patient's body. A distal end (26) of the spring-biased probe (14) is retracted within the housing in an unbiased or rest state, and extends axially outward from an axial opening (28) in the distal axial face (30) of the housing (12) upon application of the bias force on the housing. Preferably, the bias spring (24) is selected to exert a specific bias between the probe (14) and the housing (12), such that the distal end (26) of the spring-biased probe is axially displaced from the rest state to a position flush with the distal axial face (30) of the housing upon the application of a selected bias force to the housing (12), thereby providing an examiner with a tactile indication of the application of the selected bias force by the proximal end of the probe against the patient.

A method for applying a selected and repeatable force against a patient's body using a manually actuated palpometer device (10) set forth in the present disclosure requires first placing the proximal end (16) of the palpometer probe (14) in contact with a selected area on the patient's body. Grasping the palpometer housing (12) in one hand, an examiner places a thumb over the axial opening (28) in the distal axial face (30) of the housing, urging the housing axially towards the patient's body with a bias force. As the bias force on the housing is increased, the internally contained bias spring (24) is compressed between the housing and the annular flange (22) on the probe, and the distal end (26) of the probe is displaced towards the axial opening (28) in the distal axial face. Upon application of the predetermined amount of bias force, the distal end (26) of the probe is displaced to a position which is flush with the distal axial face (30) of the housing (12), providing the examiner with a tactile sensation to the thumb. By relying upon the tactile sensation caused by the displacement of the distal end (26) of the probe (14), the examiner can maintain the predetermined amount of bias force against the patient's body, and may easily apply repetitions of the same predetermined amount of bias force as required during testing of the patient's tactile or pain sensitivity, or to establish stimulus-response functions on the temporalis and masseter muscles and on the temporomandibular joint.

The foregoing features, and advantages set forth in the present disclosure as well as presently preferred embodiments will become more apparent from the reading of the following description in connection with the accompanying drawings.

BRIEF DESCRIPTION OF THE SEVERAL VIEWS OF THE DRAWINGS

In the accompanying drawings which form part of the specification:

FIG. 1 is a perspective illustration of a palpometer of the present disclosure, having a proximal probe end axially displaceable between a rest position (shown in phantom) and an application position;

FIG. 2 is a side plan view of a palpometer of the present disclosure, having a proximal probe end axially displaceable between a rest position (shown in phantom) and an application position;

FIG. 3 is a top plan view of a palpometer of the present disclosure, having a proximal probe end axially displaceable between a rest position (shown in phantom) and an application position;

Corresponding reference numerals indicate corresponding parts throughout the several figures of the drawings. It is to be understood that the drawings are for illustrating the concepts set forth in the present disclosure and are not to scale.

Figure 4:
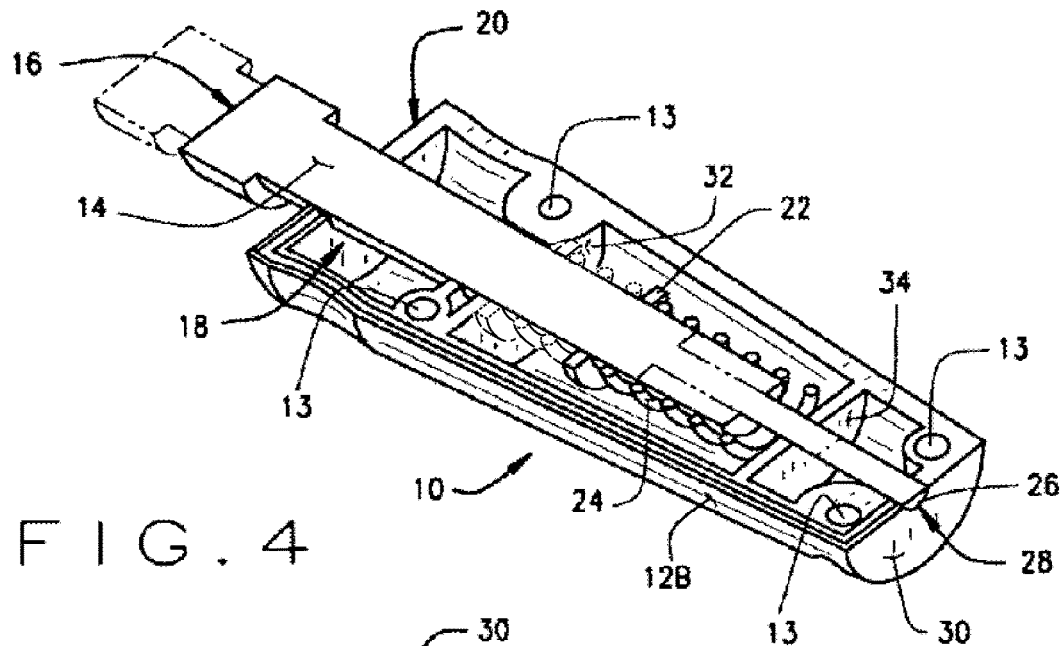
FIG. 4 is a sectional perspective view of a palpometer of the present disclosure, taken along the axial midline, having a proximal probe end axially displaceable between a rest position (shown in phantom) and an application position.

Before any embodiments of the invention are explained in detail, it is to be understood that the invention is not limited in its application to the details of construction and the arrangement of components set forth in the following description or illustrated in the drawings.

DETAILED DESCRIPTION

The following detailed description illustrates the invention by way of example and not by way of limitation. The description enables one skilled in the art to make and use the present disclosure, and describes several embodiments, adaptations, variations, alternatives, and uses of the present disclosure, including what is presently believed to be the best mode of carrying out the present disclosure.

Figure 5:
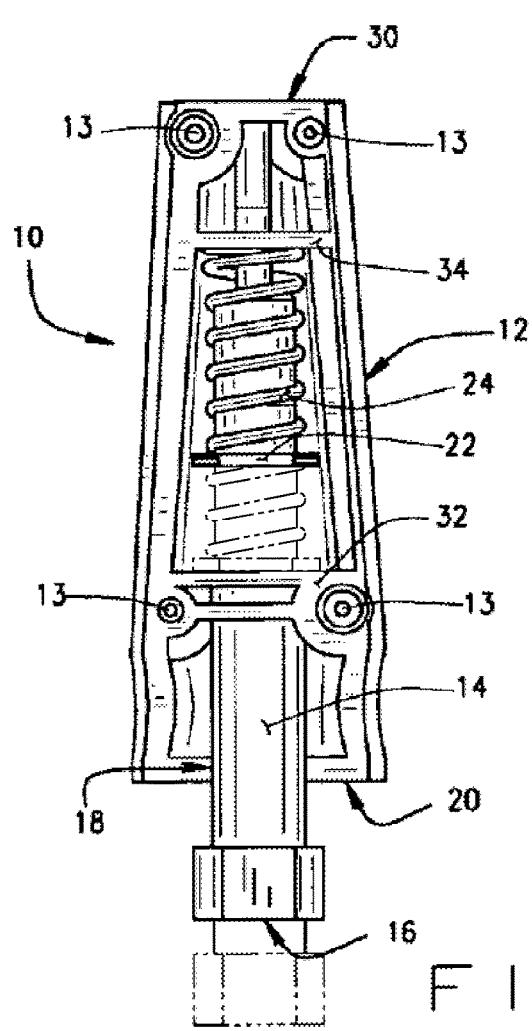
FIG. 5 is a sectional plan view of a palpometer of the present disclosure, taken along the axial midline, having a proximal probe end axially displaceable between a rest position (shown in phantom) and an application position.
Figure 6A:
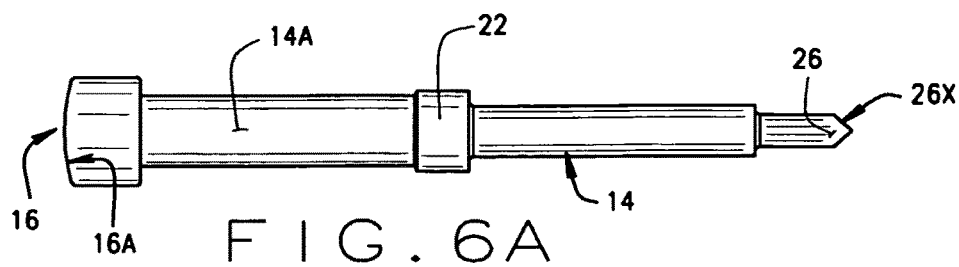
FIG. 6A is a illustration of an exemplary probe for a palpometer of the present disclosure.
Figure 6B:
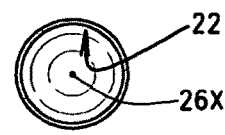
FIG. 6B is an axial view of the proximal end of the exemplary probe shown in FIG. 6A.
Figure 7:
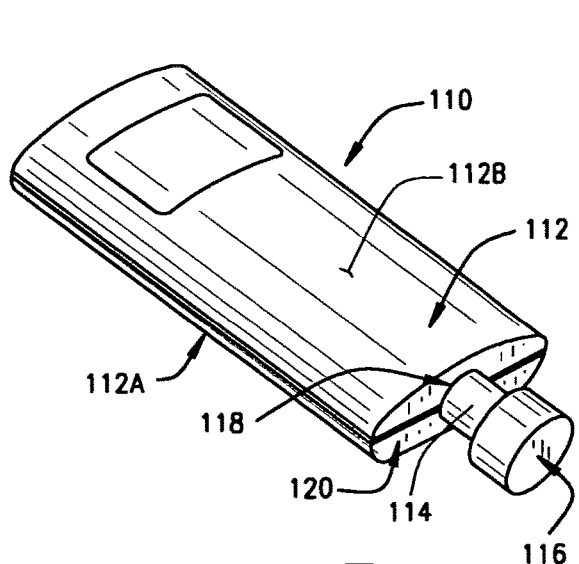
FIG. 7 is a perspective shaded illustration of a variation of the palpometer of the present disclosure, having a proximal probe end axially displaceable between a rest position (not shown) and an application position.
Figure 8:
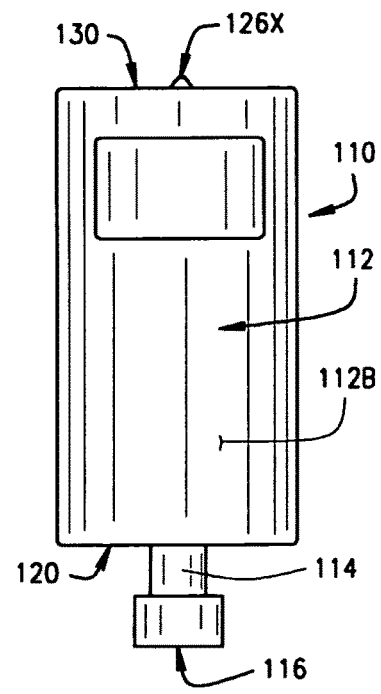
FIG. 8 is a front perspective view of the palpometer shown in FIG. 7.
Figure 9:
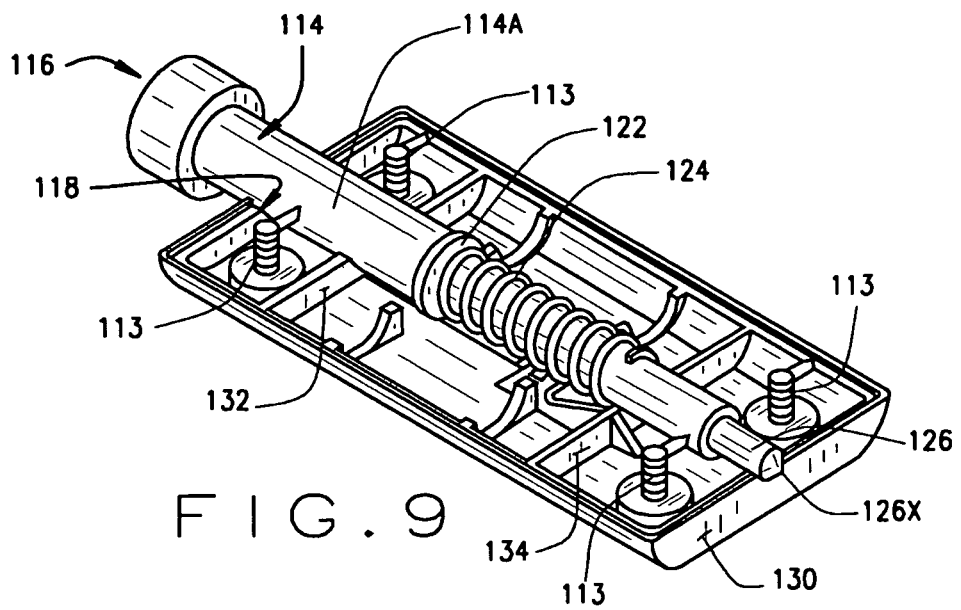
FIG. 9 is a side perspective view of the palpometer shown in FIG. 7.
Figure 10:
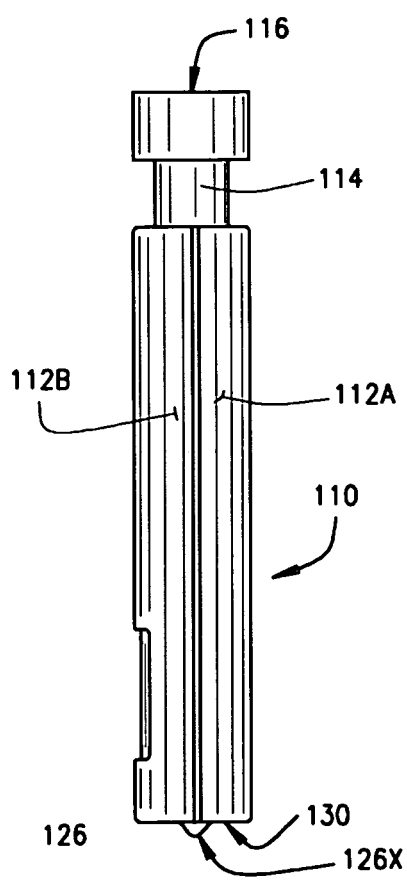
FIG. 10 is a sectional perspective view of the palpometer variation of FIG. 7, taken along the axial midline, having a proximal probe end which is axially displaceable between a rest position (not shown) and an application position.
Figure 11:
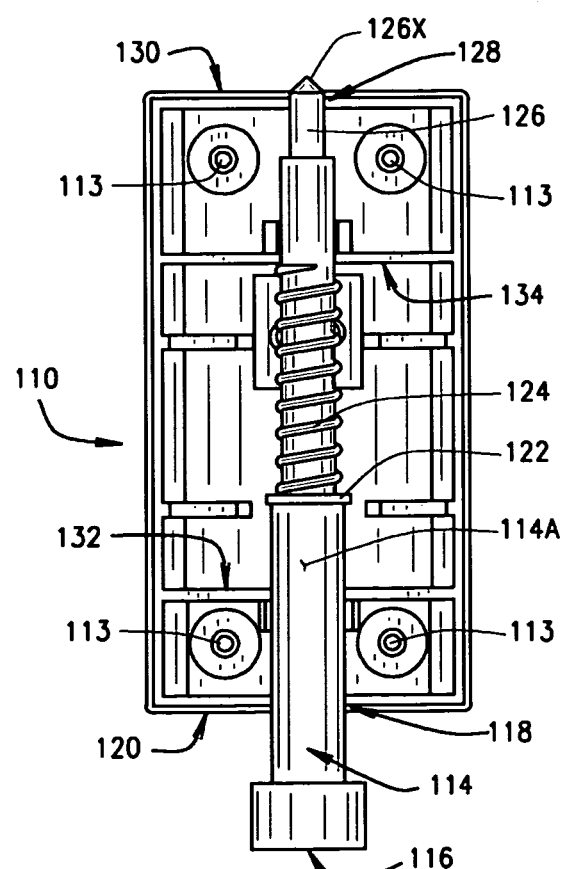
FIG. 11 is plan view of the sectional illustration shown in FIG. 10.

Turning to the Figures, a palpometer device (10) of the present disclosure for assisting an examiner to evaluate deep pain sensitivity in a patient is shown generally. The palpometer device (10) consists of a housing (12) internally supporting an axially displaceable spring-biased probe (14) for axial displacement through openings (18, 28) at opposite axial ends of the housing. The housing preferably has outer dimensions which are sized for a comfortable one-handed grip by an examiner, such as a cylindrical form (10) shown in FIGS. 1-5, or an alternate rounded rectangular form (100) shown in FIGS. 7-11, and may be formed from any suitable material such as colored plastic or metal. Other than the external shape of the housing 110, the embodiments shown in FIGS. 7-11 is substantially identical to that shown in FIGS. 1-5, and corresponding parts in the exemplary alternate embodiment will be designated with reference numbers incremented by 100.

Suitable surface coatings to facilitate comfort, appearance, or antimicrobial properties may be applied as required. Color applied to the housing (12, 112) or probe (14, 114) may be utilized to indicate palpometers (10, 110) configured to apply different predetermined forces. As shown in the Figures, the housing (12, 112) is preferably formed in two halves (12A, 12B, 112A, 112B), joined along a longitudinal axis and secured together by a plurality of fasteners (13, 113). However, those of ordinary skill in the art will recognize that the housing may be formed from any suitable material and from any number of parts without departing from the scope of the invention.

The interior of the housing (12, 112), as best seen in FIGS. 4, 5, 10, and 11 is generally hollow between the proximal end surface (20, 120) and distal axial end surface (30, 130). In order to support the spring-biased probe axially within the housing, a proximal buttress (32, 132) and a distal buttress (34, 134) are transversely disposed within the interior of the housing. Each buttress includes an axial opening for receiving the spring-biased probe.

The spring-biased probe (14, 114) consists of a generally cylindrical body (14A, with the proximal end (16, 116) defining a probe surface disposed external to the housing, and the distal end (26, 126) defining a reduced-diameter indicator. The probe surface at the proximal end (16, 116) is adapted for contact with a patients body, and may be coated or uncoated. Preferably, the proximal end of the probe includes rounded edges (16R, 116R) and has a surface area equal to 1 cm$^2$, however, those of ordinary skill in the art will recognize that different configurations and sizes for the proximal end of the probe (14, 114) may be utilized according to the particular application of the palpometer (10, 110).

The probe body (14, 114) further includes the annular flange (22, 122) or shoulder disposed generally medially between the proximal and distal ends, for axial positioning between the proximal (32, 132) and distal (34, 134) buttresses of the housing (12, 112). A bias spring (24, 124) is coaxially disposed within the housing and surrounds the probe body, between the annular flange or shoulder (22, 122) and the distal buttress (34, 134) of the housing. In a rest position, the bias spring exerts a minimal axial bias force between the annular flange or shoulder and the distal buttress of the housing, maintaining the proximal end (16, 116) of the probe in an extended position. Axial movement of the probe proximal end (16, 116) towards the extended position is limited by interference between the annular flange or shoulder (22, 122) and the proximal buttress (32, 132) within the housing.

The bias spring (24, 124) is selected to resist axial displacement of the probe (14, 114) upon the application of an axial load to probe proximal end (16, 116). Axial loads on the probe proximal end will compress the bias spring between the annular flange or shoulder (22, 122) and the distal buttress (34, 134) within the housing, displacing the probe proximal end (16, 116) axially towards the housing. Correspondingly, the axial displacement of the probe relative to the housing will cause the probe distal end (26, 126) to be axially displaced within the housing towards the opening (28, 128) in the housing distal surface (30, 130). Preferably, the bias spring is selected such that a predetermined axial load must be applied to the proximal end of the probe in order for the indicator at the distal end (26, 126) of the probe to become flush with the housing distal surface (30, 130). Excessive axial loads will result in the indicator extending axially outward from the housing distal surface, providing a tactile and visual warning to the examiner that the predetermined axial load has been exceeded. Conversely, an applied axial load which is less than the predetermined axial load will not sufficiently displace the indicator at the distal end of the probe to reach the housing distal surface.

Those of ordinary skill in the art will recognize that the specific predetermined axial load may be selected in accordance for the intended use of the palpometer. For example, axial loads on the order of 0.5 kg and 1.0 kg at the proximal end of the probe may be suitable for use when evaluating stimulus-response functions on the temporalis and masseter muscles and on the temporomandibular joint, while axial loads on the order of 2.0 kg are better suitable for evaluating arthritic patients. Axial loads on the order of 4.0 kg are suitable for patients being evaluated for fibromyalgia. In order to indicate the application of the desired axial load on the probe proximal end, the bias spring (24, 124) may be selected to have the necessary characteristics, and/or the range of axial displacement for the probe (14, 114) may be altered by varying the length of the probe body (14A, 114A), as well as the relative axial positions of the annular flange or shoulder (22, 122) and the internal buttresses (32, 34, 132, and 134) within the housing (12, 112). Alternatively, an adjustable bias spring (not shown) may be utilized to allow for selection of different axial loads as required.

A method for applying a selected and repeatable force against a patient's body using a manually actuated palpometer device (10, 110) set forth in the present disclosure requires first placing the proximal end (16, 116) of the palpometer probe (14, 114) in contact with a selected area on the patient's body. Grasping the palpometer housing (12, 112) in one hand, an examiner places a thumb over the opening (28, 128) in the distal axial face (30, 130) of the housing, urging the housing axially towards the patient's body with an axial bias force. As the bias force on the housing is increased, the internally contained bias spring (24, 124) is compressed between the distal buttress (34, 134) in the housing and the annular flange or shoulder (22, 122) on the probe body, and the distal end (26, 126) of the probe with the indicator tip is displaced towards the opening (28, 128) in the distal axial face (30, 130) of the housing. Upon application of the predetermined amount of bias force, the distal end of the probe with the indicator tip is sufficiently displaced axially within the housing to a position which is flush with the housing distal axial face, providing the examiner with a tactile sensation of contact to the thumb covering the opening. By relying upon the tactile sensation caused by the displacement of the indicator tip at the distal end of the probe, the examiner can maintain the predetermined amount of bias force against the patient's body, and may easily apply repetitions of the same predetermined amount of bias force as required during testing of the patient's tactile or pain sensitivity, such as to establish stimulus-response functions on the temporalis and masseter muscles and on the temporomandibular joint.

Those of ordinary skill in the art will recognize that the applied force may be increased slowly or quickly to reach the predetermined level of force between the proximal end and the patient's body, as is required for the particular testing regime being carried out. For example, the force may be applied quickly, reaching the predetermined limit on the order of 1-2 seconds, or slowly, over 5-10 seconds as desired by the examiner.

Tests were conducted to compare test-retest variation between manual palpation, the palpometer of the present disclosure, and a commercial electronic pressure algometer and to establish stimulus-response functions (S-R) on the temporalis and masseter muscles and temporomandibular joint (TMJ).

The test procedures involved sixteen volunteers (19-36 years) without TMD according to the RDC/TMD criteria. Manual palpation per the RDC/TMD was performed on three locations and the test subjects scored palpation pressure on a 0-10 numerical rating scales (NRS). The palpometer of the present disclosure, configured with a 1 $cm^2$ probe proximal end, based on the bias spring with a indicator tip touching the examiners hand when the correct pressure was achieved, was applied to the same locations and subjects scored perceived pain on the NRS. Finally, pressure pain thresholds were determined with a Somedic electronic pressure algometer (1 $cm^2$ probe, 30 kPa/s). All techniques were repeated five times at each location with at least two minutes of elapsed time between. The coefficient of variation (CV) was compared between locations and techniques (analysis of variance). The palpometer of the present disclosure was further used to construct S-R curves from the three locations with a 0.5, 1.0 and 2.0 kg pressure and NRS scores.

The resulting data indicated that the CV (10.4±8.6%) did not vary across locations ($P>0.260$) or between techniques ($P>0.087$). The S-R indicated the highest sensitivity on the TMJ ($P<0.001$) and consistent S-R functions with greater NRS scores at 2.0 kg compared to 1.0 kg and 0.5 kg ($P<0.001$). This concludes that the palpometer of the present disclosure provides low test-retest variability, and was able to detect differences in craniofacial sensitivity as well as to facilitate the construction of robust S-R curves.

As various changes could be made in the above constructions without departing from the scope of the disclosure, it is intended that all matter contained in the above description or shown in the accompanying drawings shall be interpreted as illustrative and not in a limiting sense.

The invention claimed is:

1. A palpometer device, comprising:
a housing, said housing having a distal end and a proximal end;
a probe supported axially within the housing by a proximal buttress and a distal buttress, for axial movement relative to said housing, said probe having a proximal end which is disposed outside an axial bore in said proximal end of said housing, a first portion of said probe adjacent to said proximal end of said probe having a first diameter and being partially contained within said housing, said probe having a distal end and a second portion adjacent to said distal end of said probe having a second diameter smaller than said first diameter, wherein said distal buttress has an opening defined therein, said opening having a diameter which is less than said first diameter;
said probe having a first position wherein said distal end of said probe is contained within said housing, a second position wherein said distal end of said probe is extended from an axial bore in said distal end of said housing, and a threshold position between said first position and said second position when said distal end of said probe is displaced flush with said distal end of said housing; and
a biasing element disposed within said housing, said biasing element biasing said probe axially towards said first position;
wherein the palpometer device is configured such that when an axial force is applied to said proximal end of said probe, said probe moves from said first position axially towards said second position relative to said housing;
wherein said probe and said biasing element are cooperatively configured such that:
said probe is in said first position when said applied axial force is less than a predetermined force threshold;
said probe is in said threshold position when said applied axial force reaches said predetermined force threshold; and
said probe is in said second position when said applied axial force exceeds said predetermined force threshold; and
wherein said threshold position is a tactile indicator indicating that said applied axial force reaches said predetermined force threshold when said distal end of said probe is at said threshold position, wherein said first portion of said probe adjacent to said proximal end of said probe having said first diameter is the same part that is partially contained within said housing.

2. The palpometer device of claim 1, wherein said biasing element is a bias spring.

3. The palpometer device of claim 2, wherein said bias spring is coaxially disposed about said probe, between an annular flange or shoulder on said probe and said distal buttress.

4. The palpometer device of claim 1, wherein said biasing element is configured in accordance with said predetermined force threshold.

5. The palpometer device of claim 1, wherein said biasing element is adjustable to select said predetermined force threshold.

6. The palpometer device of claim 1, wherein said housing is colored, said color indicative of said predetermined force threshold.

7. The palpometer device of claim 1, wherein said proximal end of said probe has a surface area of 1 cm$^2$.

8. The palpometer device of claim 1, wherein said housing is formed from plastic.

9. The palpometer device of claim 1, wherein said distal end of said probe includes an indicator tip configured to provide tactile sensation in response to said applied axial force exceeding said predetermined force threshold.

10. The palpometer device of claim 1, wherein the predetermined force threshold is in the range of 0.5 kg to 4.0 kg.

11. A method for repeatable testing of pain sensitivity in a patient using a palpometer device, comprising:
providing a palpometer device including:
a housing, said housing having a distal end and a proximal end;
a probe supported axially within the housing by a proximal buttress and a distal buttress, for axial movement relative to said housing, said probe having a proximal end which is disposed outside an axial bore in said proximal end of said housing, a first portion of said probe adjacent to said proximal end of said probe having a first diameter and being partially contained within said housing, said probe having a distal end and a second portion adjacent to said distal end of said probe having a second diameter smaller than said first diameter, wherein said distal buttress has an opening defined therein, said opening having a diameter which is less than said first diameter;
said probe having a first position wherein said distal end of said probe is contained within said housing, a second position wherein said distal end of said probe is extended from an axial bore in said distal end of said housing, and a threshold position between said first position and said second position when said distal end of said probe is displaced flush with said distal end of said housing; and
a biasing element disposed within said housing, said biasing element biasing said probe axially towards said first position;
wherein the palpometer device is configured such that when an axial force is applied to said proximal end of said probe, said probe moves from said first position axially towards said second position relative to said housing;
wherein said probe and said biasing element are cooperatively configured such that:
said probe is in said first position when said applied axial force is less than a predetermined force threshold;
said probe is in said threshold position when said applied axial force reaches said predetermined force threshold; and
said probe is in said second position when said applied axial force exceeds said predetermined force threshold; and
wherein said threshold position is a tactile indicator indicating that said applied axial force reaches said predetermined force threshold when said distal end of said probe is at said threshold position,
positioning said proximal end of said probe in contact with the patient at a selected testing location;
exerting an increasing axial force on the selected testing location through said proximal end of said probe so that the applied axial force is applied to said proximal end of said probe and said proximal end of said probe is axially displaced towards said housing;
monitoring, by tactile sensation, attainment of said probe into said threshold position; and
responsive to said probe being in said threshold position, said threshold position being the tactile indicator indicating that the applied axial force is reaching said predetermined force threshold, holding said applied axial force at said predetermined force threshold for a selected duration or terminating said applied axial force; and
monitoring a response from the patient to said applied axial force reaching said predetermined force threshold.

12. The method of claim 11, further including repeating, at least once, the steps of exerting the increasing axial force, monitoring attainment of the probe into the threshold position, holding or terminating the applied axial force, and monitoring said response from said patient.

13. The method of claim 11, wherein the predetermined force threshold is in the range of 0.5 kg to 4.0 kg.

* * * * *